United States Patent
Choulika et al.

(10) Patent No.: US 7,629,326 B2
(45) Date of Patent: Dec. 8, 2009

(54) CHROMOSOMAL MODIFICATION INVOLVING THE INDUCTION OF DOUBLE-STRANDED DNA CLEAVAGE AND HOMOLOGOUS RECOMBINATION AT THE CLEAVAGE SITE

(75) Inventors: André Choulika, Paris (FR); Richard C. Mulligan, Lincoln, MA (US)

(73) Assignees: Institut Pasteur, Paris (FR); Children's Medical Center Corporation, Boston, MA (US)

( * ) Notice: Subject to any disclaimer, the term of this patent is extended or adjusted under 35 U.S.C. 154(b) by 75 days.

(21) Appl. No.: 11/636,397

(22) Filed: Dec. 8, 2006

(65) Prior Publication Data

US 2007/0141038 A1     Jun. 21, 2007

Related U.S. Application Data

(63) Continuation of application No. 10/337,229, filed on Jan. 6, 2003, now abandoned, which is a continuation of application No. 09/917,295, filed on Jul. 27, 2001, now abandoned, which is a continuation of application No. PCT/US00/03014, filed on Feb. 3, 2000.

(60) Provisional application No. 60/118,669, filed on Feb. 3, 1999.

(51) Int. Cl.
```
A01N 43/04      (2006.01)
A01N 63/00      (2006.01)
A01N 65/00      (2006.01)
A61K 31/07      (2006.01)
C07H 21/02      (2006.01)
C07H 21/04      (2006.01)
C12N 15/00      (2006.01)
C12Q 1/68       (2006.01)
```
(52) U.S. Cl. .................... 514/44; 424/93.1; 435/320.1; 435/6; 536/23.1
(58) Field of Classification Search ........................ None
See application file for complete search history.

(56) References Cited

U.S. PATENT DOCUMENTS

| | | | |
|---|---|---|---|
| 5,436,150 A | 7/1995 | Chandrasegaran | |
| 5,674,499 A | 10/1997 | Willemse et al. | |
| 5,830,729 A | 11/1998 | Jaisser et al. | |
| 5,962,327 A | 10/1999 | Dujon et al. | |
| 6,238,924 B1 | 5/2001 | Dujon et al. | |
| 7,285,538 B2 * | 10/2007 | Choulika et al. | 514/44 |
| 2002/0110898 A1 | 8/2002 | Choulika et al. | |
| 2007/0141038 A1 * | 6/2007 | Choulika et al. | 424/93.21 |

FOREIGN PATENT DOCUMENTS

| WO | WO 96/14408 | 5/1996 |
|---|---|---|
| WO | WO 00/46385 | 8/2000 |

OTHER PUBLICATIONS

Alwin et al. (2005) Mol. Ther. 12:610-617.*
Bibikova et al. (2001) Mol. Cell. Biol. 21:289-297.*
Rubanyi (2001) Mol. Aspects Med. 22:113-142.*
Eck et al. (1996) Goodman & Gilman's The Pharmacological Basis of Therapeutics, 9th Edition, Chapter 5, McGraw-Hill, NY.*
Paques et al. (2007) Curr. Gene Ther. 7:49-66.*
Cohen-Tannoudji, M. et al., "I-SceI-Induced Gene Replacement at a Natural Locus in Embryonic Stem Cells," *Molecular and Cellular Biology*, 18(3):1444-1448 (1998).
Choulika, A. et al., "Induction of Homologous Recombination in Mammalian Chromosomes by Using the I-SceI System of Saccharomyces cerevisiae," *Molecular and Cellular Biology*, 15(4):1968-1973 (1995).
Choulika, A. et al., "The Yeast I-*Sce* I Meganuclease Induces Site-Directed Chromosomal Recombination in Mammalian Cells," C.R. Acad. Sci. Paris, Life Sciences, *Genetics*, 317:1013-1019 (1994).
Smith, J. et al., "A Detailed Study of the Substrate Specificity of a Chimeric Restriction Enzyme," *Nucleic Acids Res.*, 27(2):674-681 (1999).
Nahon, E. and Raveh, D., "Targeting a Truncated Ho-Endonuclease of Yeast to Novel DNA Sites with Foreign Zinc Fingers," *Nucleic Acids Res.*, 26(5):1233-1239 (1998).
Kim, Y.G. et al., "Hybrid Restriction Enzymes: Zinc Finger Fusions to Fok I Cleavage Domain," *Proc. Natl. Acad. Sci. USA*, 93(3):1156-1160 (1996).
Verma, I.M. et al., "Gene Therapy-promises, problems and prospects," *Nature*, 389:239-242 (1997).
Marshall, E., "Gene Therapy's Growing Pains," *Science*, 269:1050, 1052-1055 (1995).
Ross, G. et al., "Gene Therapy in the United States: A Five-Year Status Report," *Human Gene Therapy*, 7 :1781-1790 (1996).
Orkin, "Report and Recommendations of the Panel to Access the NIH Investment in Research in Gene Therapy," NIH Press, pp. 1-40 (Dec. 7, 1995).
"There are Common Motifs in Many Sequence-Specific DNA-Binding Proteins," in *Molecular Biology of the Cell*, $2_{nd}$ed., Alberts, B., et al., (edu.)(NY: Garland Publishing, Inc.) Chap. 9, 490 (1989).
Promega, Revolutions in Science, 1993/94 Catalog, p. 20.
Anderson, W.F., "Human gene therapy," *Nature*, 392 (Suppl):25-30 (1998).
Nishikawa, M. and Huang, L., "Nonviral Vectors in the New Millenium: Delivery Barriers in Gene Transfer," *Human Gene Therapy*, 12:861-870 (2001).

(Continued)

*Primary Examiner*—Robert M Kelly
(74) *Attorney, Agent, or Firm*—Hamilton Brook Smith & Reynolds, P.C.

(57) ABSTRACT

Methods of modifying, repairing, attenuating and inactivating a gene or other chromosomal DNA in a cell are disclosed. Also disclosed are methods of treating or prophylaxis of a genetic disease in an individual in need thereof. Further disclosed are chimeric restriction endonucleases.

4 Claims, 6 Drawing Sheets

OTHER PUBLICATIONS

Balicki, D., and Beutler, E., "Gene Therapy of Human Disease," *Medicine*, 81(1):69-86 (2002).

Rozenberg, Y., et al., "Alternative gene delivery," *S.T.P. Pharma Sciences*, 11(1):21-30 (2001).

Plessis, A., et al., "Site-Specific Recombination Determined by I-*Sce* l, a Mitochondrial Group I Intron-Encoded Endonuclease Expressed in the Yeast Nucleus," *Genetics 130*:451-460 (Mar. 1992).

Rouet, P., et al., "Expression of a site-specific endonuclease stimulates homologous recombination in mammalian cells," *Proc. Natl. Acad. Sci. USA:91*:6064-6068 (Jun. 1994).

Kim, Y-G., and Chandrasegaran, S., "Chimeric Restriction Endonuclease," *Proc. Natl. Acad. Sci. USA*, 91: 883-887 (1994).

* cited by examiner

| Number of β-gal expressing cells | | No homology | Super coiled | linear |
|---|---|---|---|---|
| I-SceI tagged deletion | I-SceI + | 0 | 3786 (7.5%) | 185 (0.4%) |
| | I-SceI − | 0 | 0 | 9 (0.02%) |
| Simple deletion | I-SceI + | 0 | 0 | 2 (0.004%) |
| | I-SceI − | 0 | 0 | 7 (0.01%) |

FIG. 4

| Enzyme | Organism (strain) | Size | Site Size | Cleavage | Shape of Cleavage | GenBank Accession No. | Commercially Available |
|---|---|---|---|---|---|---|---|
| ENZYMES ENCODED BY INDEPENDENT GENES | | | | | | | |
| Endo.Sce | Saccharomyces cerevisiae (IAM 4274) | 476 | 25 | very frequent | 4/3'OH | M63839 | |
| HO | Saccharomyces cerevisiae | 586 | 18 | very rare | 4/3'OH | M14678 | |
| ENZYMES ENCODED BY INTRONS | | | | | | | |
| I-Ceu I | Chlamydomonas eugametos | 218 | 20 | very rare | 4/3'OH | S15138 | Yes |
| I-Chu I | Chlamydomonas humicola | 218 | 20 | very rare | 4/3'OH | L06107 | |
| I-Cre I | Chlamydomonas reinhardtii | 163 | 24 | very rare | 4/3'OH | X01977 | |
| I-Csm I | Chlamydomonas smithii | 237 | | | | X55305 | |
| I-Dir I | Didymium iridis (Pan 2) | 244 | | | | X71792 | |
| I-Dmo I | Desulfurococcus mobilis | 194 | | rare | 4/3'OH | P21505 | |
| I-Hmu I | Bacteriophage SPO1/B. subtilis | 174 | | | | M37686 | |
| I-Hmu II | Bacteriophage SP82/B. subtilis | 187 | | | | | |
| I-Ppo I | Physarum polycephalum (Carolina) | 185 | 15 | rare | 4/3'OH | M38131 | Yes |
| I-Sce I | Saccharomyces cerevisiae (IL8-8C/R53) | 235 | 18 | very rare | 4/3'OH | P03882 | Yes |
| I-Sce II | Saccharomyces cerevisiae (D273-10B) | 316 | 15 | frequent | 4/3'OH | P03878 | |
| I-Sce III | Saccharomyces cerevisiae (777-3A) | 335 | 18 | very rare | 4/3'OH | P03877 | |
| I-Sce IV | Saccharomyces cerevisiae (777-3A) | 307 | | rare | 4/3'OH | | |
| I-Tev I | Bacteriophage T4/E. coli | 245 | 39 | ? | 2/3'OH | M12742 | |
| I-Tev II | Bacteriophage T4/E. coli | 258 | 25 | ? | 2/3'OH | | |
| I-Tev III | Bacteriophage RB3/E. coli | 269 | | | 2/5'P | X59078 | |
| INTERCALATING PROTEINS | | | | | | | |
| PI-Mle I | Mycobacterium leprae | 365 | | | | X73822 | |
| PI-Mtu I | Mycobacterium tuberculosis | 439 | | | | X58485 | |
| PI-Psp I | Pyrococcus species (GB-D) | 537 | | | | U00707 | |
| PI-Tli I | Thermococcus litoralis | 390 | 20 | rare | 4/3'OH | M74198 | Yes |
| PI-Tli II | Thermococcus litoralis | 541 | 12 | very rare | 4/3'OH | M74198 | Yes |
| PI-Sce V | Saccharomyces cerevisiae (YFG 499) | 454 | 12 | very rare | 4/3'OH | M21609 | Yes |

FIG. 5

CHROMOSOMAL MODIFICATION INVOLVING THE INDUCTION OF DOUBLE-STRANDED DNA CLEAVAGE AND HOMOLOGOUS RECOMBINATION AT THE CLEAVAGE SITE

RELATED APPLICATIONS

This application is a continuation of U.S. application Ser. No. 10/337,229, filed Jan. 6, 2003 now abandoned, which is a continuation of U.S. application Ser. No. 09/917,295, filed Jul. 27, 2001 now abandoned, which is a continuation of International Application No. PCT/US00/03014, which designated the United States and was filed on Feb. 3, 2000, published in English, which claims the benefit of U.S. Provisional Application No. 60/118,669, filed Feb. 3, 1999. The entire teachings of the above applications are incorporated herein by reference.

BACKGROUND OF THE INVENTION

Homologous recombination provides a method for genetically modifying chromosomal DNA sequences in a precise way. In addition to the possibility of introducing small precise mutations in order to alter the activity of the chromosomal DNA sequences, such a methodology makes it possible to correct the genetic defects in genes which can cause disease. Unfortunately, current methods for achieving homologous recombination are inherently inefficient, in that homologous recombination-mediated gene repair can usually be achieved in only a small proportion of cells that have taken up the relevant "targeting or correcting" DNA. For example, in cultured mammalian cells, such recombinational events usually occur in only one in ten thousand cells which have taken up the relevant targeting or correcting DNA.

Thus, there is a need to develop new and improved methods of homologous recombination-mediated gene repair.

SUMMARY OF THE INVENTION

The present invention is related to Applicants' discovery that induction of double stranded DNA cleavage at a specific site in chromosomal DNA induces a cellular repair mechanism which leads to highly efficient recombinational events at that locus. As a result, Applicants' invention relates to methods which result in induction in cells of double stranded DNA cleavage at a specific site in chromosomal DNA. In one embodiment, induction of a double stranded break at a site of interest in chromosomal DNA of the cell is accompanied by the introduction of a targeting DNA homologous to the region surrounding the cleavage site, which results in the efficient introduction of the targeting DNA into the locus. In a second embodiment, induction of a double stranded break at a site of interest in chromosomal DNA of the cell leads to introduction of chromosomal DNA homologous to the region surrounding the site of interest into the site of interest via gene conversion.

The present invention relates to a method of repairing a specific sequence of interest in chromosomal DNA of a cell comprising (a) inducing in the cell a double stranded break at a site of interest, and (b) introducing into the cell targeting DNA, wherein the targeting DNA comprises (1) DNA homologous to the region surrounding the site of interest and (2) DNA which repairs the specific sequence of interest upon recombination between the targeting DNA and the chromosomal DNA. The targeting DNA is introduced into the cell under conditions appropriate for introduction of the targeting DNA into the site of interest. In a second embodiment, the method of repairing a specific sequence of interest in chromosomal DNA of a cell comprises inducing in the cell double stranded cleavage at a site of interest under conditions appropriate for chromosomal DNA homologous to the region surrounding the site of interest to be introduced into the site of interest and repair of the specific sequence of interest.

In a particular embodiment, the specific sequence of interest is a mutation.

The present invention also relates to a method of modifying a specific sequence in chromosomal DNA of a cell comprising (a) inducing in the cell double stranded cleavage at a site of interest in the specific sequence to be modified, and (b) introducing into the cell targeting DNA, wherein the targeting DNA comprises (1) DNA homologous to the region surrounding the site of interest and (2) DNA which modifies the specific sequence upon recombination between the targeting DNA and the chromosomal DNA. The targeting DNA is introduced into the cell under conditions appropriate for introduction of the targeting DNA into the site of interest. In a second embodiment, the method of modifying a specific sequence in chromosomal DNA of a cell comprises inducing in the cell double stranded cleavage at a site of interest in the specific sequence to be modified under conditions appropriate for chromosomal DNA homologous to the region surrounding the site of interest to be introduced into the site of interest and modification of the specific sequence.

The invention further relates to a method of attenuating an endogenous gene of interest in a cell comprising (a) inducing in the cell double stranded cleavage at a site of interest in the endogenous gene of interest, and (b) introducing into the cell targeting DNA, wherein the targeting DNA comprises (1) DNA homologous to the region surrounding the site of interest and (2) DNA which attenuates the gene of interest upon recombination between the targeting DNA and the gene of interest. The targeting DNA is introduced into the cell under conditions appropriate for introduction of the targeting DNA into the site of interest.

The invention relates to a method of introducing a mutation into a site of interest in chromosomal DNA of a cell comprising (a) inducing in the cell double stranded cleavage at the site of interest, and (b) introducing into the cell targeting DNA, wherein the targeting DNA comprises (1) DNA homologous to the region surrounding the site of interest and (2) the mutation to be introduced into the chromosomal DNA. The targeting DNA is introduced into the cell under conditions appropriate for introduction of the targeting DNA into the site of interest.

The invention also relates to a method for treating or prophylaxis of a genetic disease in an individual in need thereof comprising (a) inducing in cells of the individual double stranded cleavage at a site of interest, and (b) introducing into the individual targeting DNA, wherein the targeting DNA comprises (1) DNA homologous to the region surrounding the site of interest and (2) DNA which repairs the site of interest upon recombination between the targeting DNA and the chromosomal DNA. The targeting DNA is introduced into the individual under conditions appropriate for introduction of the targeting DNA into the site of interest. In a second embodiment the method for treating or prophylaxis of a genetic disease in an individual in need thereof comprises inducing in cells of the individual double stranded cleavage at a site of interest under conditions appropriate for chromosomal DNA homologous to the region surrounding the site of interest to be introduced into the site of interest and repair of the site of interest. Alternatively, cells can be removed from an individual to be treated, modified by the present method and introduced into the individual.

The invention relates to a method of correcting a genetic lesion in chromosomal DNA of a cell comprising inducing in the cell double stranded cleavage at a site of interest in the genetic lesion under conditions appropriate for chromosomal DNA homologous to the region surrounding the site of interest to be introduced into the site of interest and correct the genetic lesion. Here, too, the method can be carried out in cells present in an individual or in cells removed from the individual, modified and then returned to the individual (ex vivo).

Double stranded breaks (cleavages) at a site of interest can be achieved by restriction endonucleases or chemical entities which recognize and cleave the site of interest. Double stranded breaks at a site of interest can also be achieved by the chimeric restriction endonucleases of the invention.

The invention also relates to chimeric restriction endonucleases produced by linking DNA binding sequence(s) and DNA cleavage domains. DNA binding sequences include zinc finger binding domains and meganuclease recognition sites. DNA cleavage domains include restriction endonuclease cleavage domains. Nucleic acid molecules which encode the chimeric restriction endonucleases of the invention and host cells which comprise the nucleic acid molecules of the invention are also included in the invention.

The present invention further relates to the resulting cells and their uses, such as for treatment or prophylaxis of a condition or disorder in an individual (e.g., a human or other mammal or vertebrate). For example, cells can be produced (e.g., ex vivo) by the method described herein and then introduced into an individual using known methods. Alternatively, cells can be modified in the individual (without being removed from the individual).

BRIEF DESCRIPTION OF THE DRAWINGS

FIG. 4 is a table which provides the results from I-SceI meganuclease-mediated gene conversion experiments.

FIG. 5 is a table providing examples of meganuclease enzymes.

DETAILED DESCRIPTION OF THE INVENTION

Figure 1:
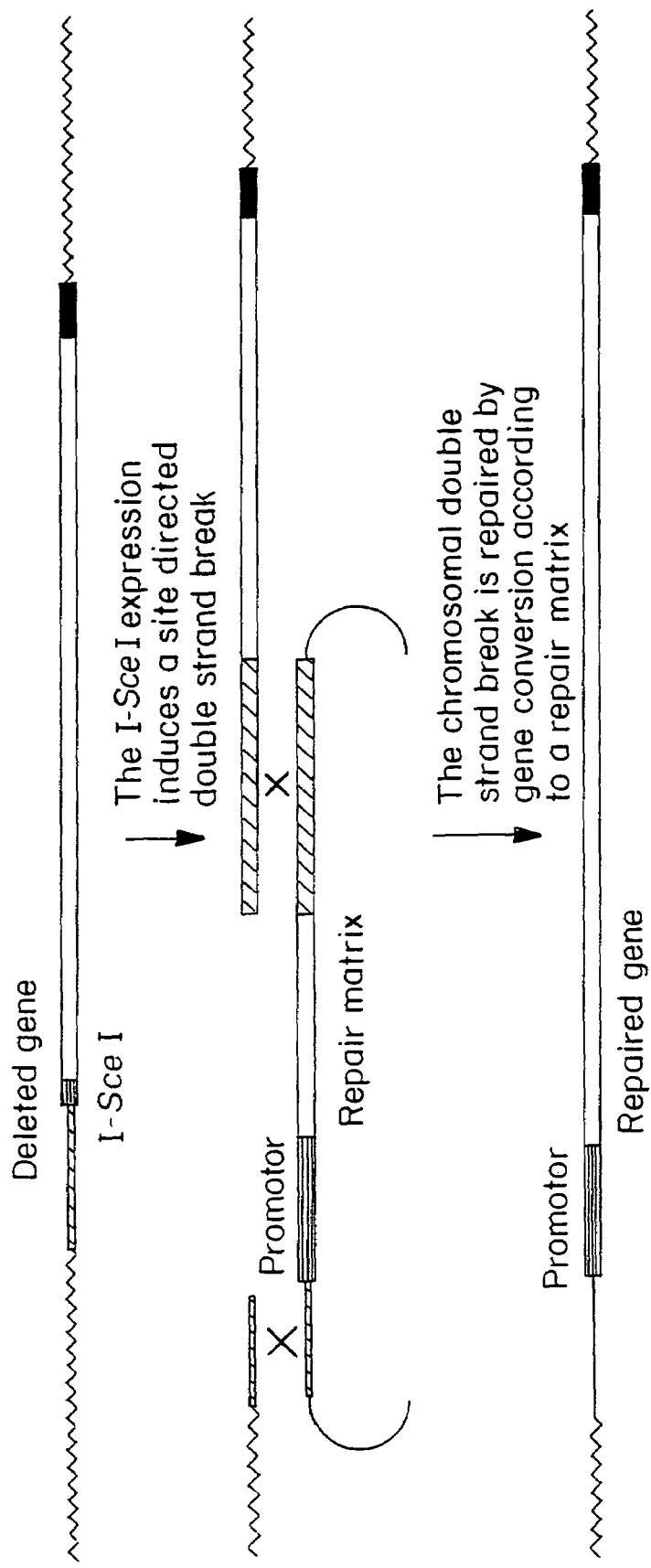
FIGS. 1 and 2 are schematic diagrams illustrating an experiment to measure gene conversion efficiency in vivo by I-SceI-induced gene activation.

The present invention is based on Applicants' discovery that induction of double stranded DNA cleavage at a specific site in chromosomal DNA induces a cellular repair mechanism which leads to highly efficient recombinational events at that locus. Frequencies of homologous recombination can be stimulated 1,000 fold and can lead to the introduction of specific genetic modifications in approximately 10% of transfected cells (uncorrected for transfection efficiencies) using the methods described herein. The introduction of the double stranded break is achieved, for example, by a restriction endonuclease which recognizes the site of interest. In one embodiment of the invention, the introduction of the double stranded break is accompanied by the introduction of a targeting segment of DNA homologous to the region surrounding the cleavage site, which results in the efficient introduction of the targeting sequences into the locus (either to repair a genetic lesion or to alter the chromosomal DNA in some specific way). In a second embodiment of the invention, the induction of a double stranded break at a site of interest is employed to obtain correction of a genetic lesion via a gene conversion event in which the homologous chromosomal DNA sequences from the other copy of the gene donates sequences to the sequences where the double stranded break was induced. This latter strategy leads to the correction of genetic diseases in which either one copy of a defective gene causes the disease phenotype (such as occurs in the case of dominant mutations) or in which mutations occur in both alleles of the gene, but at different locations (as is the case of compound heterozygous mutations). Large segments of DNA can be altered by this method, so it is possible to repair even large deletions of chromosomal DNA. Targeting DNA (or targeting segment of DNA) homologous to the region surrounding the cleavage site is also referred to herein as a repair matrix.

Double stranded breaks (cleavages) at a site of interest can be achieved by restriction endonucleases or chemical entities which recognize and cleave the site of interest. Examples of chemical entities which recognize and cleave a site of interest are described by Dervan et al., for example, in U.S. Pat. Nos. 4,665,184, 4,942,227, 4,795,700, and 5,789,155, which references are incorporated in their entirety herein by reference. Double stranded breaks at a site of interest can also be achieved by the chimeric restriction endonucleases of the invention, as described herein.

A restriction endonuclease site can be inserted into genomic DNA of a cell at a site of interest by either gene targeting through homologous recombination or by random insertion using a variety of methods. Examples of suitable methods include microinjection of naked DNA, stable calcium phosphate precipitation, transfection and using recombinant retroviruses. Insertion of a restriction endonuclease site can be achieved by the selection of cells that have inserted the restriction endonuclease site into a place (locus or site) of interest and in the proper copy number. Selection can be done by using a reporter gene that can be popped out after analysis of the modified cells. The term "reporter gene", as used herein, refers to a nucleic acid sequence whose product can be easily assayed, for example, calorimetrically as an enzymatic reaction product, such as the lacZ gene which encodes for β-galactosidase. The reporter gene can be operably linked to a suitable promoter so that expression of the reporter gene can be used to assay integration of the restriction endonuclease site into the genome of a cell. Examples of widely-used reporter molecules include enzymes such as β-galactosidase, β-glucoronidase, β-glucosidase; luminescent molecules such as green flourescent protein and firefly luciferase; and auxotrophic markers such as His3p and Ura3p. (See, e.g., Chapter 9 in Ausubel, F. M., et al. *Current Protocols in Molecular Biology*, John Wiley & Sons, Inc. (1998)). Depending on the cellular target, cells can be used for reimplantation into an animal, in tissue culture or to produce transgenic animal by reimplantation to produce chimeras. Restriction endonuclease site (e.g., I-Sce I site) containing constructs can be injected into a fertilized egg in order to produce a transgenic animal.

To insert a restriction endonuclease site into the genomic DNA of a cell at a site of interest by targeting through homologous recombination, the restriction endonuclease site is inserted into a targeting DNA molecule, which comprises DNA homologous to a genomic cellular target of interest. Preferably, the homologous DNA is at least about 4 to about 6 kb long and can be designated as the left and right arms of the targeting DNA construct. A restriction endonuclease site and an expression cassette allowing for the selection of the resulting recombinant cells are inserted between the two homologous arms. In a particular embodiment, the expression cassette can be the neomycin resistance gene (neo) operably linked to the Pgk promoter and including the polyadenylation site of the SV40 virus at the 3' end. The cassette is bounded by two direct repeated loxP sites of the P1 phage for a post-selection excision step of the cassette. Geneticin resistant clones (Geneticin resistance is the result of the expression of the neo cassette) can be evaluated for proper targeting by polymerase chain reaction (PCR) on genomic DNA of the resistant clones and by Southern blot analysis. Targeted cells are then treated with the Cre protein of the P1 phage to induce the loss of the floxed resistance cassette. As a result, cells bearing one I-SceI site at the proper location are obtained. Targeted cells can be cells that are used to produce recombinant molecules or embryonic stem cells (ESC) that are used to produce transgenic animals by injection of the ESC into blastocysts and reimplantion of blastocysts into a foster mother. These animals can be used for recombinant protein production or as models for diseases.

A restriction endonuclease used in the present invention recognizes a target DNA sequence (e.g., a restriction endonuclease site) which would not lead to death of the cells upon cleavage of the DNA sequence by the restriction endonuclease. A meganuclease enzyme, which recognizes a very large DNA sequence, is an example of a restriction endonuclease which can be used in the present invention. An example of a meganuclease enzyme is I-SceI, which recognizes an 18-bp site (DNA sequence) that does not appear to be represented in murine or human DNA. Other examples of meganuclease enzymes are provided in FIG. 5. Other meganuclease enzymes (natural and synthetic) are known and described in the art. In a particular embodiment, a restriction endonuclease used in the present invention has a specificity of at least $6.7 \times 10^{-10}$ of cleaving (cutting) frequency. A restriction endonuclease used in the present invention can be introduced into a cell or individual as the restriction endonuclease itself or as a vector comprising a nucleic acid which encodes the restriction endonuclease.

A model chromosomal locus was generated in which a site for the meganuclease I-SceI was introduced within the target region for recombination, and double stranded DNA cleavage via introduction of a vector encoding the restriction endonuclease was induced. For application of the method to the manipulation of any chromosomal DNA locus, chimeric restriction endonucleases generated by the juxtaposition of specific DNA binding sequences (in some cases generated by the linking of specific zinc finger binding domains) and DNA cleavage domains can be used to elicit cleavage, either by introduction of an appropriate expression construct, the enzyme, or an RNA encoding the enzyme. In the case of direct introduction of enzyme, enzyme domains can be coupled to facilitators of protein entry into cells, such as tat, HSV VP22, or anthrax toxin. A functional chimeric restriction enzyme containing a domain which recognizes the I-SceI recognition site and a cleavage domain from FokI enzyme was generated. In another embodiment, chemical entities capable of recognizing and cleaving a specific chromosomal site can be used to induce recombination.

The present invention relates to a method of repairing a specific sequence of interest in chromosomal DNA of a cell comprising (a) inducing in the cell a double stranded break at a site of interest, and (b) introducing into the cell targeting DNA, wherein the targeting DNA comprises (1) DNA homologous to the region surrounding the site of interest and (2) DNA which repairs the specific sequence of interest upon recombination between the targeting DNA and the chromosomal DNA. The targeting DNA is introduced into the cell under conditions appropriate for introduction of the targeting DNA into the site of interest. In a second embodiment, the method of repairing a specific sequence of interest in chromosomal DNA of a cell comprises inducing in the cell double stranded cleavage at a site of interest under conditions appropriate for chromosomal DNA homologous to the region surrounding the site of interest to be introduced into the site of interest and repair of the specific sequence of interest.

In a method of repairing a specific sequence of interest in chromosomal DNA of a cell, in a particular embodiment, the targeting DNA is designed to include (1) DNA homologous to chromosomal DNA adjacent to the specific sequence of interest, wherein the homologous DNA is sufficient for recombination between the targeting DNA and chromosomal DNA, and (2) DNA which repairs the specific sequence of interest upon recombination between the targeting DNA and chromosomal DNA. Typically, the homologous DNA of the targeting DNA construct flanks each end of the DNA which repairs the specific sequence of interest. That is, the homologous DNA is at the left and right arms of the targeting DNA construct and the DNA which repairs the sequence of interest is located between the two arms.

In a particular embodiment, the specific sequence of interest is a mutation. Thus, in this embodiment, the invention relates to a method of repairing a mutation in chromosomal DNA of a cell comprising (a) inducing in the cell a double stranded break at a site of interest, and (b) introducing into the cell targeting DNA, wherein the targeting DNA comprises (1) DNA homologous to the region surrounding the site of interest and (2) DNA which repairs the mutation upon recombination between the targeting DNA and the chromosomal DNA. The targeting DNA is introduced into the cell under conditions appropriate for introduction of the targeting DNA into the site of interest. In a second embodiment, the method of repairing a mutation in chromosomal DNA of a cell comprises inducing in the cell double stranded cleavage at a site of interest under conditions appropriate for chromosomal DNA homologous to the region surrounding the site of interest to be introduced into the site of interest and repair of the mutation.

In a method of repairing a mutation in chromosomal DNA of a cell, in a particular embodiment, the targeting DNA is designed to include (1) DNA homologous to chromosomal DNA adjacent to the mutation, wherein the homologous DNA is sufficient for recombination between the targeting DNA and chromosomal DNA, and (2) DNA which repairs the mutation upon recombination between the targeting DNA and chromosomal DNA. Typically, the homologous DNA of the targeting DNA construct flanks each end of the DNA which repairs the mutation. That is, the homologous DNA is at the left and right arms of the targeting DNA construct and the DNA which repairs the mutation is located between the two arms.

As used herein, a mutation refers to a nucleotide change, such as a single or multiple nucleotide substitution, deletion or insertion, in a nucleotide sequence. Preferably, the mutation is a point mutation. Chromosomal DNA which bears a mutation has a nucleic acid sequence that is different in sequence from that of the corresponding wildtype chromosomal DNA.

As used herein, chromosomal DNA adjacent to a specific sequence of interest refers to chromosomal DNA present near or next to the specific sequence of interest.

The present invention also relates to a method of modifying a specific sequence (or gene) in chromosomal DNA of a cell comprising (a) inducing in the cell double stranded cleavage at a site of interest in the specific sequence to be modified, and (b) introducing into the cell targeting DNA, wherein the targeting DNA comprises (1) DNA homologous to the region surrounding the site of interest and (2) DNA which modifies the specific sequence upon recombination between the targeting DNA and the chromosomal DNA. The targeting DNA is introduced into the cell under conditions appropriate for introduction of the targeting DNA into the site of interest. In a second embodiment, the method of modifying a specific sequence in chromosomal DNA of a cell comprises inducing in the cell double stranded cleavage at a site of interest in the specific sequence to be modified under conditions appropriate for chromosomal DNA homologous to the region surrounding the site of interest to be introduced into the site of interest and modification of the specific sequence.

In a method of modifying a specific sequence (or gene) in chromosomal DNA of a cell, in a particular embodiment, the targeting DNA is designed to include (1) DNA homologous to the specific sequence (or gene) to be modified, wherein the homologous DNA is sufficient for recombination between the targeting DNA and chromosomal DNA, and (2) DNA which modifies the specific sequence (or gene) upon recombination between the targeting DNA and the chromosomal DNA. Typically, the homologous DNA of the targeting DNA construct flanks each end of the DNA which modifies the specific sequence (or gene). That is, the homologous DNA is at the left and right arms of the targeting DNA construct and the DNA which modifies the specific sequence (or gene) is located between the two arms.

The invention further relates to a method of attenuating an endogenous gene of interest in a cell comprising (a) inducing in the cell double stranded cleavage at a site of interest in the endogenous gene of interest, and (b) introducing into the cell targeting DNA, wherein the targeting DNA comprises (1) DNA homologous to the region surrounding the site of interest and (2) DNA which attenuates the gene of interest upon recombination between the targeting DNA and the gene of interest. The targeting DNA is introduced into the cell under conditions appropriate for introduction of the targeting DNA into the site of interest.

In a method of attenuating or inactivating an endogenous gene of interest in a cell, in a particular embodiment, the targeting DNA is designed to include (1) DNA homologous to a target site of the endogenous gene of interest, wherein the homologous DNA is sufficient for recombination between the targeting DNA and the gene of interest, and (2) DNA which attenuates or inactivates the gene of interest upon recombination between the targeting DNA and the gene of interest. Typically, the homologous DNA of the targeting DNA construct flanks each end of the DNA which attenuates or inactivates the gene of interest. That is, the homologous DNA is at the left and right arms of the targeting DNA construct and the DNA which attenuates or inactivates the gene of interest is located between the two arms.

The invention relates to a method of introducing a mutation into a site of interest in chromosomal DNA of a cell comprising (a) inducing in the cell double stranded cleavage at the site of interest, and (b) introducing into the cell targeting DNA, wherein the targeting DNA comprises (1) DNA homologous to the region surrounding the site of interest and (2) the mutation to be introduced into the site of interest. The targeting DNA is introduced into the cell under conditions appropriate for introduction of the targeting DNA into the site of interest.

In a method of introducing a mutation into a target site (or gene) of chromosomal DNA of a cell, in a particular embodiment, the targeting DNA is designed to include (1) DNA homologous to the target site (or gene), wherein the homologous DNA is sufficient for recombination between the targeting DNA and the chromosomal DNA, and (2) the mutation which is introduced into the chromosomal DNA upon recombination between the targeting DNA and the chromosomal DNA. Typically, the homologous DNA of the targeting DNA construct flanks each end of the mutation. That is, the homologous DNA is at the left and right arms of the targeting DNA construct and the mutation to be introduced into the chromosomal DNA (i.e., into a target site or gene) is located between the two arms.

The invention also relates to a method for treating or prophylaxis of a genetic disease in an individual in need thereof comprising (a) inducing in cells of the individual double stranded cleavage at a site of interest, and (b) introducing into the individual targeting DNA, wherein the targeting DNA comprises (1) DNA homologous to the region surrounding the site of interest and (2) DNA which repairs the site of interest. The targeting DNA is introduced into the individual under conditions appropriate for introduction of the targeting DNA into the site of interest. In a second embodiment the method for treating or prophylaxis of a genetic disease in an individual in need thereof comprises inducing in cells of the individual double stranded cleavage at a site of interest under conditions appropriate for chromosomal DNA homologous to the region surrounding the site of interest to be introduced into the site of interest.

The invention relates to a method of correcting a genetic lesion in chromosomal DNA of a cell comprising inducing in the cell double stranded cleavage at a site of interest in the genetic lesion under conditions appropriate for chromosomal DNA homologous to the region surrounding the site of interest to be introduced into the site of interest.

The invention also relates to the generation of animal models of disease in which restriction endonuclease sites (e.g., I-SceI target sites) are introduced at the site of the disease gene for evaluation of optimal delivery techniques.

The invention further relates to chimeric restriction endonucleases generated by the juxtaposition of specific DNA binding sequence(s) and DNA cleavage domain(s). These chimeric restriction endonucleases can be manufactured according to methods generally known in the art. For example, the DNA binding sequence(s) and DNA cleavage domain(s) can be produced as separate "components", which are than joined (linked) using known methods or can be produced as a single continuous unit. For example, the chimeric restriction endonucleases can be manufactured by chemical synthesis or recombinant DNA/RNA technology (see, e.g., Sambrook et al., Eds., *Molecular Cloning: A Laboratory Manual,* 2nd edition, Cold Spring Harbor University Press, New York (1989); and Ausubel et al., Eds., *Current Protocols In Molecular Biology,* John Wiley & Sons, New York (1998). In a particular embodiment, chimeric restriction endonucleases capable of recognizing specific DNA sequences unique to a disease allele can be generated through juxtaposition of zinc finger DNA binding domains and restriction endonuclease cleavage domains.

DNA binding sequences include zinc finger binding domains and meganuclease recognition sites. DNA cleavage domains include restriction endonuclease cleavage domains. Thus, in a particular embodiment, the chimeric restriction endonuclease is generated by the linking of specific zinc finger binding domains and DNA cleavage domains. In another embodiment, the chimeric restriction endonuclease is generated by joining a meganuclease recognition site and a restriction endonuclease cleavage domain. In a further embodiment, the chimeric restriction endonuclease is produced by joining a I-SceI meganuclease recognition site and the FokI cleavage domain.

The phrases "site of interest", "target site" and "specific site", as used herein, refer to a distinct chromosomal location at which a double stranded break (cleavage) is to be induced, thereby inducing a cellular repair mechanism which leads to highly efficient recombinational events at that locus.

Targeting DNA and/or restriction endonucleases introduced into a cell or individual as described above can be inserted in a vector. As used herein, a "vector" includes a nucleic acid vector, e.g., a DNA vector, such as a plasmid, a RNA vector, virus or other suitable replicon (e.g., viral vector).

Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

A vector comprising a nucleic acid encoding a restriction endonuclease contains all or part of the coding sequence for the restriction endonuclease operably linked to one or more expression control sequences whereby the coding sequence is under the control of transcription signals to permit production or synthesis of the restriction endonuclease. Such expression control sequences include promoter sequences, enhancers, and transcription binding sites. Selection of the promoter will generally depend upon the desired route for expressing the restriction endonuclease. The elements can be isolated from nature, modified from native sequences or manufactured de novo (e.g., by chemical synthesis or recombinant DNA/RNA technology, according to methods known in the art (see, e.g., Sambrook et al., Eds., *Molecular Cloning: A Laboratory Manual*, 2nd edition, Cold Spring Harbor University Press, New York (1989); and Ausubel et al., Eds., *Current Protocols In Molecular Biology*, John Wiley & Sons, New York (1997)). The elements can then be isolated and fused together by methods known in the art, such as exploiting and manufacturing compatible cloning or restriction sites.

Similarly, a vector comprising targeting DNA homologous to the region surrounding the cleavage site can be manufactured according to methods generally known in the art. For example, the vector comprising targeting DNA can be manufactured by chemical synthesis or recombinant DNA/RNA technology (see, e.g., Sambrook et al., Eds., *Molecular Cloning, A Laboratory Manual*, 2nd edition, Cold Spring Harbor University Press, New York, 1989; and Ausubel et al., Eds., *Current Protocols In Molecular Biology*, John Wiley & Sons, New York, 1994-1997).

Vectors comprising targeting DNA and/or nucleic acid encoding a restriction endonuclease can be introduced into a cell by a variety of methods (e.g., transformation, transfection, direct uptake, projectile bombardment, using liposomes). Examples of suitable methods of transfecting or transforming cells include calcium phosphate precipitation, electroporation, microinjection, infection, lipofection and direct uptake. Such methods are described in more detail, for example, in Sambrook et al., *Molecular Cloning: A Laboratory Manual*, Second Edition, Cold Spring Harbor University Press, New York (1989); and Ausubel, et al., *Current Protocols in Molecular Biology*, John Wiley & Sons, New York (1998), the teachings of which are incorporated herein by reference.

A vector comprising targeting DNA and/or nucleic acid encoding a restriction endonuclease can also be introduced into a cell by targeting the vector to cell membrane phospholipids. For example, targeting of a vector of the present invention can be accomplished by linking the vector molecule to a VSV-G protein, a viral protein with affinity for all cell membrane phospholipids. Such a construct can be produced using methods well known to those practiced in the art.

Restriction endonucleases can be introduced into a cell according to methods generally known in the art which are appropriate for the particular restriction endonuclease and cell type. For example, a restriction endonuclease can be introduced into a cell by direct uptake, microinjection, calcium phosphate precipitation, electroporation, infection, and lipofection. Such methods are described in more detail, for example, in Sambrook et al., *Molecular Cloning: A Laboratory Manual*, Second Edition, Cold Spring Harbor University Press, New York (1989); and Ausubel, et al., *Current Protocols in Molecular Biology*, John Wiley & Sons, New York (1998). Other suitable methods are also described in the art. The restriction endonuclease can be coupled to a facilitator of protein entry to facilitate introduction of the enzyme into a cell. Examples of facilitators of protein entry include tat, HSV VP22 and anthrax toxin. Coupling of a protein to a facilitator of protein entry can be accomplished using methods well known to those practiced in the art. Protein delivery strategies (e.g., HSV VP22, anthrax toxin) can be evaluated in accordance with the methods of the invention described herein.

Once in the cell, the restriction endonuclease and the vector comprising targeting DNA and/or nucleic acid encoding a restriction endonuclease are imported or translocated by the cell from the cytoplasm to the site of action in the nucleus.

As used herein, a cell refers to a prokaryotic cell, such as a bacterial cell, or eukaryotic cell, such as an animal, plant or yeast cell. A cell which is of animal or plant origin can be a stem cell or somatic cell. Suitable animal cells can be of, for example, mammalian, avian or invertebrate origin. Examples of mammalian cells include human (such as HeLa cells), bovine, ovine, porcine, murine (such as embryonic stem cells), rabbit and monkey (such as COSI cells) cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

The cells can be obtained commercially or from a depository or obtained directly from an individual, such as by biopsy. The cells used can be obtained from an individual to whom they will be returned or from another/different individual of the same or different species. For example, nonhuman cells, such as pig cells, can be modified to include a DNA construct and then introduced into a human. Alternatively, the cell need not be isolated from the individual where, for example, it is desirable to deliver the vector to the individual in gene therapy.

As used herein, the term "individual" includes mammals, as well as other animals (e.g., birds, fish, reptiles, insects). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminents (e.g., cows, pigs, horses).

Restriction endonucleases and vectors which comprise targeting DNA homologous to the region surrounding the cleavage site and/or nucleic acid encoding a restriction endonuclease can be introduced into an individual using routes of administration generally known in the art (e.g., parenteral, mucosal, nasal, injection, systemic, implant, intraperitoneal, oral, intradermal, transdermal (e.g., in slow release polymers), intramuscular, intravenous including infusion and/or bolus injection, subcutaneous, topical, epidural, buccal, rectal, vaginal, etc.). The restriction endonucleases and vectors can, preferably, be administered in a pharmaceutically acceptable carrier, such as saline, sterile water, Ringer's solution, and isotonic sodium chloride solution. The mode of administration is preferably at the location of the target cells.

The dosage of restriction endonuclease or vector of the present invention administered to an individual, including frequency of administration, will vary depending upon a variety of factors, including mode and route of administration; size, age, sex, health, body weight and diet of the recipient; nature and extent of symptoms of the disease or disorder being treated; kind of concurrent treatment, frequency of treatment, and the effect desired.

The present invention will now be illustrated by the following examples, which are not to be considered limiting in any way.

EXAMPLES

Example 1

Plasmid Construction

All DNA manipulations used standard techniques and procedures. Such methods are described, for example, in Sambrook et al., *Molecular Cloning: A Laboratory Manual*, Second Edition, Cold Spring Harbor University Press, New York (1989); and Ausubel, et al., *Current Protocols in Molecular Biology*, John Wiley & Sons, New York (1998). All synthetic oligonucleotides were synthesized on automated instruments using standard techniques.

The pPytknBWSacZ plasmid was constructed by inserting the oligonucleotide 5'-GATCATGCATAGGGATAA-CAGGGTAATAGCT-3' (SEQ ID NO:1), paired with 5'-ATTACCCTGTTATCCCTATGCAT-3' (SEQ ID NO:2), between the BclI-SacI restriction sites of the pPytknlslacZ plasmid (Henry et al., *C. R. Acad. Sci. III*, 322(12):1061-1070 (1999)). Insertion of the BclI and SacI restriction sites resulted in destruction of the BclI and the SacI restriction sites and insertion of an NsiI restriction site and an I-SceI restriction site.

The p-SlacB plasmid was constructed as follows: First, the pPytknlslacZ plasmid was digested with the SpeI and HindIII restriction enzymes, resulting in excision from the plasmid of a 578 bp fragment containing the ATG start codon and 178 bp at the 5' end of the coding region of the nlslacZ gene. The 5' extensions of the SpeI-HindIII restriction sites of the pPytknlslacZ plasmid were converted to blunt ends by a filling-in reaction using T4 DNA polymerase. The blunted ends were then ligated together to produce the p-SlacZ plasmid. The p-SlacZ plasmid was digested with the NheI and BglII restriction enzymes, resulting in excision from the plasmid of the 0.6 kb fragment containing the stop codon and SV40 polyadenylation signal at the 3' end of the nlslacZ gene. The 5' extensions of the NheI-BglII restriction sites of the p-SlacZ plasmid were converted to blunt ends by a filling-in reaction using T4 DNA polymerase. The blunted ends were then ligated together. The result is the p-SlacB plasmid comprising a nlslacZ gene with deletion of the ATG start codon, 178 bp at the 5' end, the stop codon and the SV40 polyadenylation signal. As a result of the deletion of the start codon and 178 bp at the 5' end of the coding region, nlslacZ gene expression is inactivated.

The p-BlacS plasmid was constructed as follows: First, the pPytknlslacZ plasmid was digested with the SpeI and BclI restriction enzymes after demethylation of the plasmid, resulting in excision from the plasmid of a 1.9. kb fragment. The 5' extensions of the SpeI-BclII restriction sites of the pPytknlslacZ plasmid were converted to blunt ends by a filling-in reaction using T4 DNA polymerase. The blunted ends were then ligated together to produce the p-BlacZ plasmid. The p-BlacZ plasmid was digested with the SacI and BglII restriction enzymes, resulting in excision from the plasmid of a 1.5 kb fragment. The 5' extensions of the SacI-BglII restriction sites of the pPytknlslacZ plasmid were converted to blunt ends by a filling-in reaction using T4 DNA polymerase. The blunted ends were then ligated together. The result is the p-BlacS plasmid containing a 0.6 kb fragment of the nlslacZ gene filling the exact gap contained in the pPytknBWSacZ plasmid.

The p-BlacB plasmid was constructed as follows: First, the pPytknlslacZ plasmid was digested with the SpeI and BclI restriction enzymes after demethylation of the plasmid, resulting in excision from the plasmid of a 1.9 kb fragment. The 5' extensions of the SpeI-BclII restriction sites of the pPytknlslacZ plasmid were converted to blunt ends by a filling-in reaction using T4 DNA polymerase. The blunted ends were then ligated together to produce the p-BlacZ plasmid. The p-BlacZ plasmid was digested with the NheI and BglII restriction enzymes, resulting in excision from the plasmid of a 0.6 kb fragment. The 5' extensions of the NheI-BglII restriction sites of the pPytknlslacZ plasmid were converted to blunt ends by a filling-in reaction using T4 DNA polymerase. The blunted ends were then ligated together. The result is the p-SlacB plasmid.

The p-SlacS plasmid was constructed as follows: First, the pPytknlslacZ plasmid was digested with the SpeI and HindIII restriction enzymes, resulting in excision from the plasmid of a 578 bp fragment containing the ATG start codon and 178 bp at the 5' end of the coding region of the nlslacZ gene. The 5' extensions of the SpeI-HindIII restriction sites of the pPytknlslacZ plasmid were converted to blunt ends by a filling-in reaction using T4 DNA polymerase. The blunted ends were then ligated together. The p-BlacZ plasmid was digested with the SacI and BglII restriction enzymes, resulting in excision of a 1.5 kb fragment from the plasmid. The 5' extensions of the SacI-BglII restriction sites of the p-BlacZ plasmid were converted to blunt ends by a filling-in reaction using T4 DNA polymerase. The blunted ends were then ligated together. The result is the p-SlacS plasmid containing a 0.6 kb fragment of the nlslacZ gene filling the exact gap contained in the pPytknBWSacZ plasmid.

Linearized fragments of the plasmids used in the experiments described herein were obtained by digesting the plasmids with ScaI restriction enzyme and purifying the fragments by agarose gel electrophoresis.

The p-lac plasmid was constructed as follows: First, the pPytknlslacZ plasmid was digested with the SpeI and HindIII restriction enzymes, resulting in excision from the plasmid of a 578 bp fragment containing the ATG start codon and 178 bp at the 5' end of the coding region of the nlslacZ gene. The 5' extensions of the SpeI-HindIII restriction sites of the pPytknlslacZ plasmid were converted to blunt ends by a filling-in reaction using T4 DNA polymerase. The blunted ends were then ligated together to produce the p-lacZ plasmid. The p-lacZ plasmid was digested with the NheI and BglII restriction enzymes, resulting in excision from the plasmid of the 0.6 kb fragment containing the stop codon and SV40 polyadenylation signal at the 3' end of the nlslacZ gene. The 5' extensions of the NheI-BglII restriction sites of the pWnlslacZ plasmid were converted to blunt ends by a filling-in reaction using T4 DNA polymerase. The blunted ends were then ligated together. The result is the p-lac plasmid in which the nlslacZ gene with the ATG start codon, 178 bp at the 5' end, stop codon and SV40 polyadenylation signal deleted, is not bounded at the 5' or 3' end by a I-SceI site. As a result of the deletion of the start codon and 178 bp at the 5' end of the coding region, nlslacZ gene expression is inactivated.

The pCMV I-SceI(+) and pCMV I-SceI(−) plasmids are described in Choulika et al., *C. R. Acad. Sci. III*, 317(11): 1013-1019 (1994).

The pUSVneo plasmid is described in Choulika et al., *J. Virol.*, 70(3):1792-1798 (1996).

Example 2

Cell Line Production

Five µg of the pPytknBWSacZ plasmid and 5 µg of the pUSVneo plasmid were cotransfected in 5×10⁴ NIH 3T3 cells (American Type Culture Collection) in a 35 mm petri dish (Falcon) using the CaPO₄ precipitation method. Forty-eight (48) hours after transfection, the tissue culture medium was supplemented with 600 µg/ml of Geneticin (Gibco BRL). Antibiotic selection was maintained during selection of Geneticin resistant clones and during subcloning. Twenty-four (24) Geneticin resistant clones were isolated and grown independently in Dulbecco's modified Eagle's Medium (DMEM), 10% calf serum, for 15 days before evaluating for the presence of the nlslacZ gene.

To evaluate for presence of the nlslacZ gene, DNA was extracted from cells in all 24 cultures of Geneticin resistant clones. Fragments of the nlslacZ gene were amplified by polymerase chain reaction (PCR) as described in *BioFeedback in BioTechniques*, Vol. 10, No. 1, p. 56 T, Hanley & J. P. Merlie (1991). Twenty-four (24) of 24 clones were positive for the presence of the nlslacZ gene.

Eighteen (18) of the 24 clones positive for the presence of the nlslacZ gene were evaluated for expression of the mutated nlslacZ gene. To evaluate for expression of the mutated nlslacZ gene, RNA was extracted from cells in the corresponding 18 cultures of Geneticin resistant clones. RNA encoding the mutated nlslacZ gene was amplified by reverse transcriptase polymerase chain reaction (RT-PCR). The oligonucleotide primer 5'-TACACGCGTCGTGATT-AGCGCCG-3' (SEQ ID NO:3) was used for lacZ reverse transcription. PCR was performed as described in *BioFeedback in BioTechniques*, Vol. 10, No. 1, p. 56T, Hanley & J. P. Merlie (1991). Eleven (11) of 18 clones showed a positive reaction.

Southern blot analysis of the genomic DNA of these 11 clones was performed and 3 clones were shown to have less than 3 intact copies of the pPytknlslacZDBcl construct.

Histochemical analysis of these 3 clones was performed by X-Gal staining as described in Bonnerot et al., *Methods in Enzymology, GuideTo Techniques In Mouse Development*, Academic Press, pp. 451-469 (1993). No clones showed expression of β-galactosidase. Northern blot analysis of the mRNA expressed by the integrated pPytknBWSacZ construct showed no expression for one of the clones and signals for the other two clones These two cell lines, NIH 3T3 Gap1 and NIH 3T3 Gap2, were selected to be the targets to the gap repair.

Example 3

Ex Vivo Recombination In NIH 3T3 Gap1 And NIH 3T3 Gap2 Cell Lines

Three sets of experiments were performed, in triplicate, using the NIH 3T3 Gap1 and NIH 3T3 Gap2 cell lines. Each set of experiments, in triplicate, comprises 8 different cotransfections of DNA mixes as shown in Table 1. Transfections were performed in either 5×10⁴ NIH 3T3 Gap1 cells or 5×10⁴ NIH 3T3 Gap2 cells in a 60 mm petri dish (Falcon) by the CaPO₄ precipitation method.

TABLE 1

| Mix Number | Expression Plasmid | Quantity | Repair Matrix | Quantity |
|---|---|---|---|---|
| 1 | pCMV I-SceI(+) | 9 µg | pSlacB | 1 µg |
| 2 | pCMV I-SceI(+) | 9 µg | pBlacS | 1 µg |
| 3 | pCMV I-SceI(+) | 9 µg | pSlacS | 1 µg |
| 4 | pCMV I-SceI(+) | 9 µg | pBlacB | 1 µg |
| 5 | pCMV I-SceI(−) | 9 µg | pSlacB | 1 µg |
| 6 | pCMV I-SceI(−) | 9 µg | pBlacS | 1 µg |
| 7 | pCMV I-SceI(−) | 9 µg | pSlacS | 1 µg |
| 8 | pCMV I-SceI(−) | 9 µg | pBlacB | 1 µg |

In a second set of experiments, plasmids were linearized with ScaI restriction enzyme prior to transfection. Three sets of experiments were performed, in triplicate, using the NIH 3T3 Gap1 and NIH 3T3 Gap2 cell lines. Each set of experiments, in triplicate, comprises 8 different cotransfections of DNA mixes as shown in Table 2. Transfections were performed in either 5×10⁴ NIH 3T3 Gap1 cells or 5×10⁴ NIH 3T3 Gap2 cells in a 60 mm petri dish (Falcon) by the CaPO₄ precipitation method.

TABLE 2

| Mix Number | Expression Plasmid | Quantity | Repair Matrix | Quantity |
|---|---|---|---|---|
| 9 | pCMV I-SceI(+) | 9 µg | pSlacB-li | 1 µg |
| 10 | pCMV I-SceI(+) | 9 µg | pBlacS-li | 1 µg |
| 11 | pCMV I-SceI(+) | 9 µg | pSlacS-li | 1 µg |
| 12 | pCMV I-SceI(+) | 9 µg | pBlacB-li | 1 µg |
| 13 | pCMV I-SceI(−) | 9 µg | pSlacB-li | 1 µg |
| 14 | pCMV I-SceI(−) | 9 µg | pBlacS-li | 1 µg |
| 15 | pCMV I-SceI(−) | 9 µg | pSlacS-li | 1 µg |
| 16 | pCMV I-SceI(−) | 9 µg | pBlacB-li | 1 µg |

96 hours after transfection, cells were stained for β-galactosidase expression in X-Gal and blue colony forming units (bcfu) were counted. The number of bcfu is the result of the D-loop correction in each of the experiment. Results are shown in FIG. 4.

Transfection of NIH 3T3 Gap1 cells with the mix number 1 (PCMV I-SceI(+), 9 µg; pSlacB, 1 µg) gave 12 to 28% β-galactosidase positive clones (out of the three experiments) as the higher rate of gap repair recombination of the pPytkn-BWSacZ deleted plasmid. Thus, after transfection of $1 \times 10^5$ cells with mix number 1, 96 individual cells were cloned by limit dilution according to standard methods. Cells were grown DMEM, 10% calf serum, and analyzed for β-galactosidase expression. Two (2) of 86 clones showed cells expressing β-galactosidase (10% of expression for clone 1 and 40% of expression for clone 2). Southern blot analysis of these 2 clones showed that 100% of the cells had in their nlslacZ gene recovered the deleted fragment. The lack of correspondence between the expression of the intact nlslacZ open reading frame and the total repair of the genome is probably the result of transgene variegation.

Example 4

Meganuclease-Mediated Gene Conversion

The cell lines, NIH 3T3 Gap1 and NIH 3T3 Gap2, were selected to be the targets to the gap repair. In these cells, the lacZ-Gap gene is transcribed but β-galactosidase expression is not detected (β-gal$^-$ cells). β-gal$^-$ cells are transfected with the plac plasmid and an expression vector coding for I-SceI endonuclease. The I-SceI endonuclease induces a double stranded break in the genomic target and the missing sequences are inserted into the lacZ gene by double stranded break gap repair. As a result, these cells contain a pPyt-knlslacZ plasmid that expresses β-galactosidase (β-gal$^+$ cells). A schematic diagram of this experiment is depicted in FIG. 1.

Example 5

Measure of Gene Conversion Efficiency In Vivo By I-SceI-Induced Gene Activation

Figure 2:
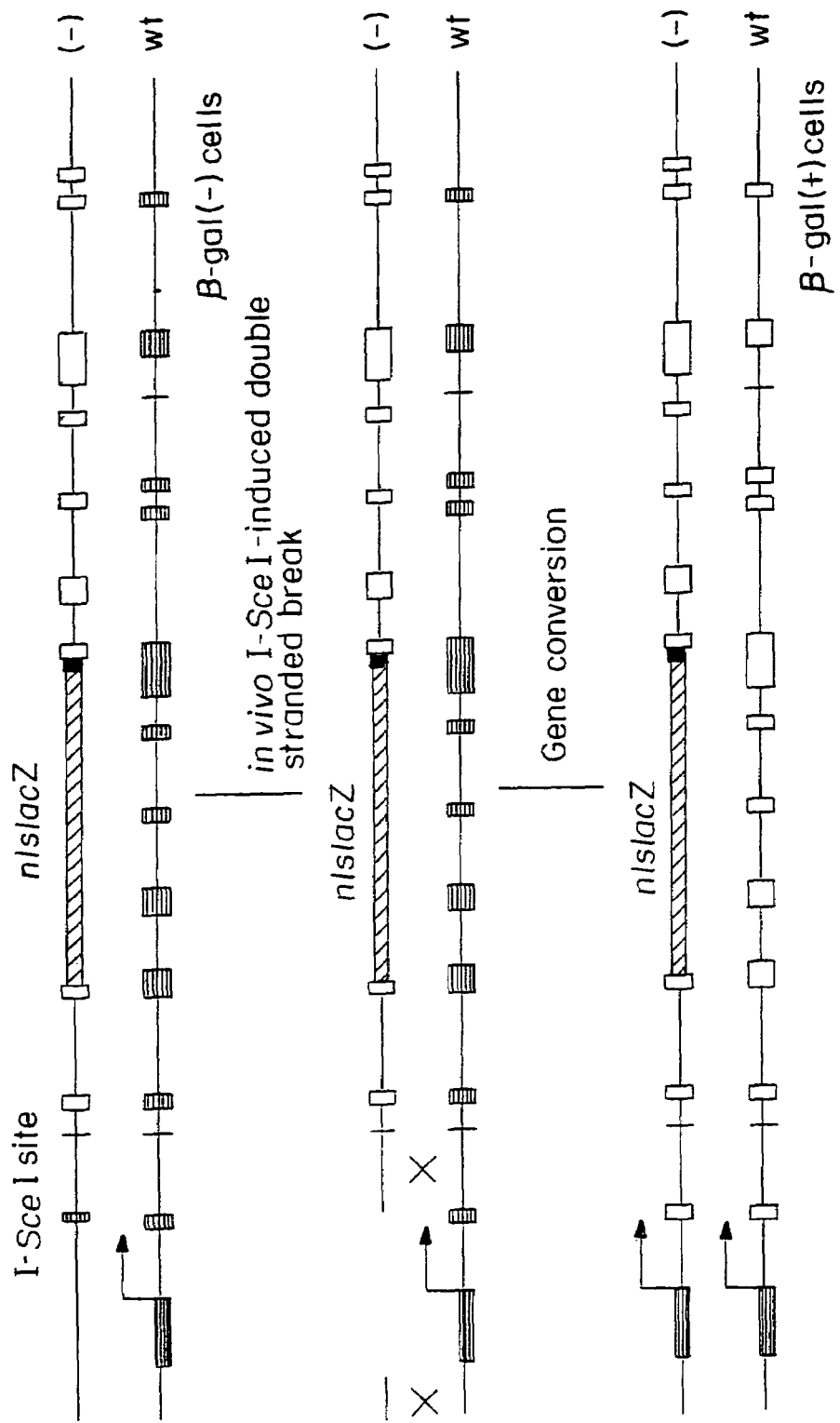
Figure 3:
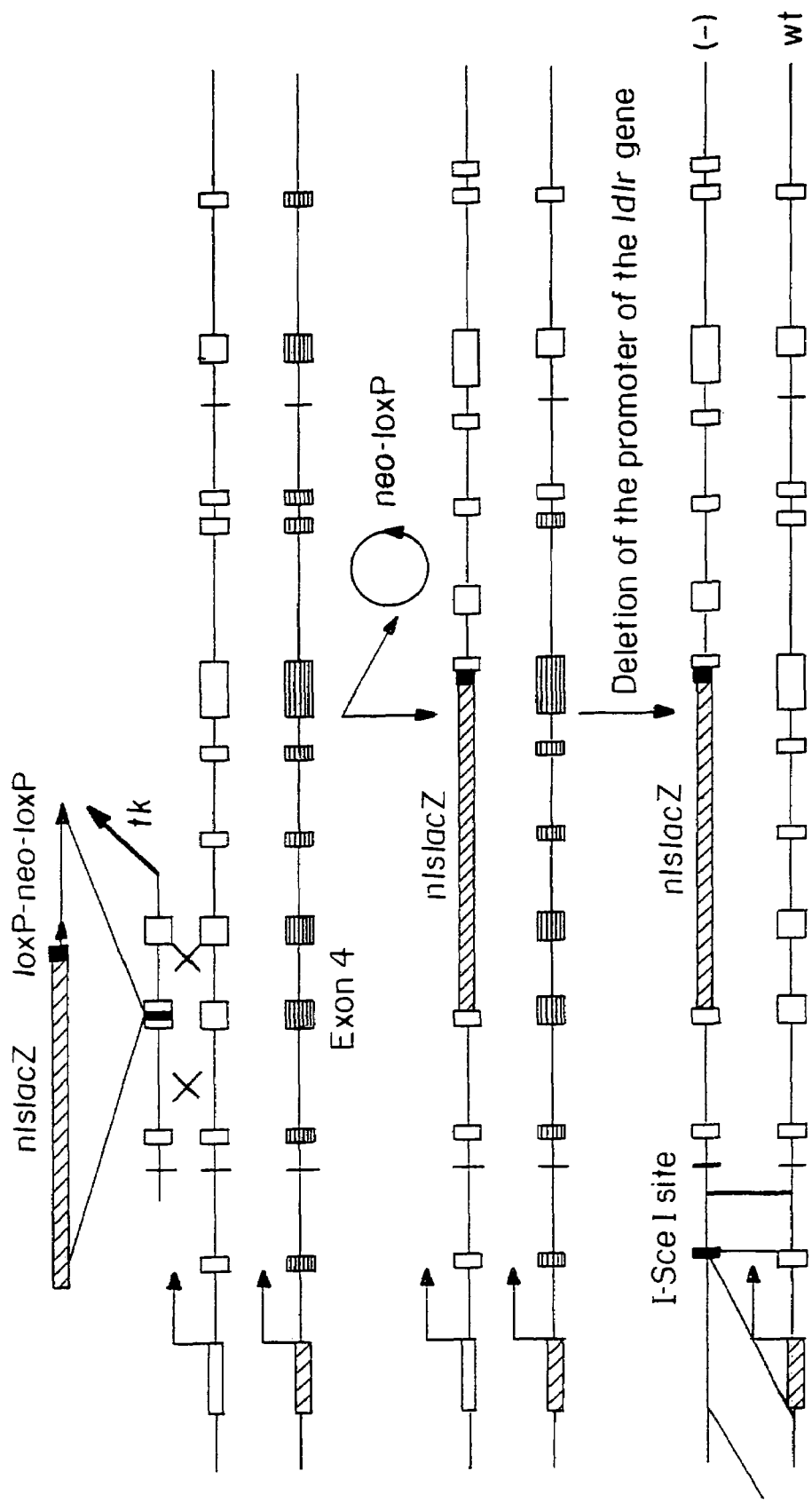
FIG. 3 is a schematic diagram illustrating the measure of the gene conversion efficiency from meganuclease-mediated gene conversion experiments.
Figure 6:
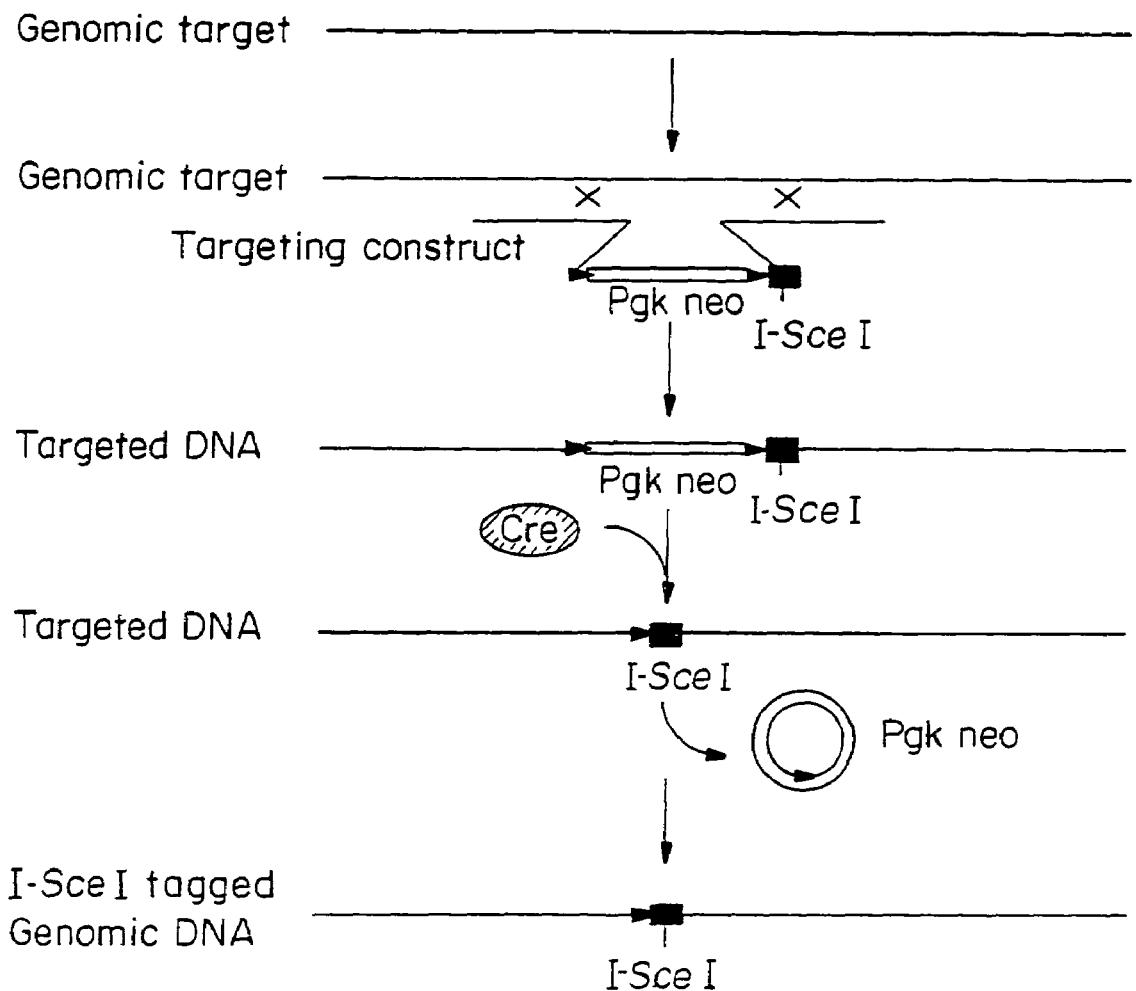
FIG. 6 is a schematic diagram illustrating a method of inserting an I-SceI site in genomic DNA.

A schematic diagram of an experiment to measure gene conversion efficiency in vivo by I-SceI-induced gene activation is depicted in FIGS. 2 and 3. A schematic diagram of the two alleles of the low density lipoprotein receptor (ldlr) gene in the mouse cellular genome is also depicted in FIGS. 2 and 3.

The nlslacZ gene with a Pgkneo cassette which is flanked on both ends by loxP sites in the same direct repeat orientation (to allow the selection of the recombined cells) is inserted into exon 4 of the ldlr gene by homologous recombination. This insertion inactivates the ldlr gene (indicated in the figures as (–), compared to (wt) for wildtype). The Pgkneo cassette is an expression cassette including the neomycin resistance gene (neo) which is operably linked to the Pgk promoter and has a SV40 polyadenylation site at the 3' end. The floxed neo cassette is excised into the recombinant cells by the expression of the Cre protein.

The 5' end of the ldlr gene on the (–) allele is replaced by homologous recombination with an I-SceI site as described above. This deletion results in the loss of the promoter and exon 1 of the ldlr gene. As a result, expression of the lac Z gene inserted into exon 4 of this allele does not occur since there is no promoter to activate its expression. Accordingly, there is no β-galactosidase activity, resulting in β-gal$^-$ cells.

In vivo induction of a double stranded break by the I-SceI meganuclease induces a double stranded break in place of the ldlr promoter of the (–) allele. Repair of the double stranded break is performed by gene conversion using the wildtype (wt) allele as a repair matrix. As a result of the double stranded break gap repair, the ldlr promoter and exon 1 are inserted in the (–) allele. Accordingly, transcription and expression of the nlslacZ gene occurs, resulting in β-galactosidase positive cells (β-gal$^+$).

The teachings of all the articles, patents and patent applications cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of repairing a specific sequence comprising a I-SceI recognition site in chromosomal DNA of a cell in vitro, comprising the steps of:
    (a) inducing in the chromosomal DNA of the cell a double stranded cleavage by a chimeric restriction endonuclease at a site of interest in the specific sequence, said site of interest comprising a I-SceI recognition site, said chimeric restriction endonuclease comprising a I-SceI DNA binding domain and a FokI DNA cleavage domain; and
    (b) introducing targeting DNA into the cell under conditions appropriate for introduction of the targeting DNA into the site of interest, wherein said targeting DNA comprises (1) DNA homologous to the region surrounding the site of interest and (2) DNA which repairs the specific sequence upon recombination between said targeting DNA and the chromosomal DNA.

2. A method of modifying a specific sequence comprising a I-SceI recognition site in chromosomal DNA of a cell in vitro, comprising the steps of:
    (a) inducing in the chromosomal DNA of the cell a double stranded cleavage by a chimeric restriction endonuclease at a site of interest in the specific sequence to be modified, said site of interest comprising a I-SceI recognition site, said chimeric restriction endonuclease comprising a I-SceI DNA binding domain and a FokI DNA cleavage domain; and
    (b) introducing targeting DNA into the cell under conditions appropriate for introduction of the targeting DNA into the site of interest, wherein said targeting DNA comprises (1) DNA homologous to the region surrounding the site of interest and (2) DNA which modifies the specific sequence upon recombination between said targeting DNA and the chromosomal DNA.

3. A method of attenuating an endogenous gene comprising a I-SceI recognition site in a cell in vitro, comprising the steps of:
    (a) inducing in the gene a double stranded cleavage at I-SceI recognition site by a I-SceI/Foki restriction endonuclease, said chimeric restriction endonuclease comprising a I-SceI DNA binding domain and a FokI DNA cleavage domain; and
    (b) introducing targeting DNA into the cell under conditions appropriate for introduction of the targeting DNA into the gene, wherein said targeting DNA comprises (1) DNA homologous to the region surrounding the I-SceI recognition site and (2) DNA which attenuates the gene upon recombination between said targeting DNA and the gene.

4. A method of introducing a mutation into a site of interest comprising a I-SceI recognition site in chromosomal DNA of a cell in vitro, comprising the steps of:
    (a) inducing in the chromosomal DNA of the cell a double stranded cleavage at the site of interest by a chimeric restriction endonuclease comprising a I-SceI DNA binding domain and a FokI DNA cleavage domain; and
    (b) introducing targeting DNA into the cell under conditions appropriate for introduction of the targeting DNA into the site of interest, wherein said targeting DNA comprises (1) DNA homologous to the region surrounding the site of interest and (2) the mutation to be introduced into the site of interest.

* * * * *

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 1
gatcatgcat agggataaca gggtaatagc t                              31

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 2
```

```
attaccctgt tatccctatg cat                                                    23

<210> SEQ ID NO 3
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 3
tacacgcgtc gtgattagcg ccg                                                    23
```